US012780911B2

(12) United States Patent
Imhof et al.

(10) Patent No.: US 12,780,911 B2
(45) Date of Patent: Nov. 3, 2026

(54) GLYCOSYLATED POLYPEPTIDES

(71) Applicant: FRESENIUS KABI DEUTSCHLAND GMBH, Bad Homburg (DE)

(72) Inventors: Markus O. Imhof, Bad Homburg (DE); Parul Gupta, Bad Homburg (DE); Adrian Blackburn, Bad Homburg (DE); Hilary Metcalfe, Bad Homburg (DE)

(73) Assignee: FRESENIUS KABI DEUTSCHLAND GMBH, Bad Homburg (DE)

( * ) Notice: Subject to any disclaimer, the term of this patent is extended or adjusted under 35 U.S.C. 154(b) by 1191 days.

(21) Appl. No.: 17/781,688

(22) PCT Filed: Dec. 11, 2020

(86) PCT No.: PCT/EP2020/085741

§ 371 (c)(1),
(2) Date: Jun. 1, 2022

(87) PCT Pub. No.: WO2021/116398

PCT Pub. Date: Jun. 17, 2021

(65) Prior Publication Data

US 2023/0049145 A1 Feb. 16, 2023

(30) Foreign Application Priority Data

Dec. 12, 2019 (EP) .................................... 19215729

(51) Int. Cl.

| | |
|---|---|
| ***C07D 401/04*** | (2006.01) |
| ***C07K 14/435*** | (2006.01) |
| ***C07K 14/475*** | (2006.01) |
| ***C07K 14/52*** | (2006.01) |
| ***C07K 14/575*** | (2006.01) |
| ***C07K 14/705*** | (2006.01) |
| ***C07K 16/18*** | (2006.01) |
| ***C07K 16/22*** | (2006.01) |
| ***C07K 16/24*** | (2006.01) |
| ***C07K 16/26*** | (2006.01) |
| ***C07K 16/28*** | (2006.01) |
| ***C12N 1/00*** | (2006.01) |
| ***C12N 5/00*** | (2006.01) |
| ***C12P 21/00*** | (2006.01) |

(52) U.S. Cl.

CPC .......... *C07K 16/241* (2013.01); *C07D 401/04* (2013.01); *C07K 14/435* (2013.01); *C07K 14/475* (2013.01); *C07K 14/52* (2013.01); *C07K 14/575* (2013.01); *C07K 14/705* (2013.01); *C07K 16/18* (2013.01); *C07K 16/22* (2013.01); *C07K 16/26* (2013.01); *C07K 16/28* (2013.01); *C12N 5/00* (2013.01); *C12P 21/005* (2013.01); *C07K 2317/14* (2013.01); *C07K 2317/40* (2013.01); *C07K 2317/41* (2013.01); *C07K 2319/30* (2013.01)

(58) Field of Classification Search

CPC ..... C07D 401/04; C12P 21/005; C07K 16/18; C07K 16/22; C07K 16/24; C07K 16/26; C07K 16/28; C07K 2317/41; C07K 16/14; C07K 14/435; C07K 14/475; C07K 14/52; C07K 14/575; C07K 14/705; C07K 2317/40; C07K 2319/30; C12N 15/63; C12N 2500/00; C12N 2500/30; C12N 2501/00; C12N 2533/20

See application file for complete search history.

(56) References Cited

U.S. PATENT DOCUMENTS

| | | | | |
|---|---|---|---|---|
| 2007/0092521 | A1* | 4/2007 | McPherson | A61P 5/14 530/391.1 |
| 2019/0194303 | A1 | 6/2019 | Wong et al. | |
| 2022/0177818 | A1* | 6/2022 | Matuszczyk | C07K 1/16 |

FOREIGN PATENT DOCUMENTS

| | | | |
|---|---|---|---|
| EP | 0206892 | B1 | 12/1991 |
| EP | 2409989 | A1 | 1/2012 |
| EP | 2806892 | B1 | 3/2019 |

OTHER PUBLICATIONS

Kuhne et al. The Impact of Immunoglobulin G1 Fc Sialylation on Backbone Amide H/D Exchange. Antibodies 8: 49, Oct. 2019 (23 total pages).*

Yang et al. Glycan Remodeling of Human Erythropoietin (EPO) Through Combined Mammalian Cell Engineering and Chemoenzymatic Transglycosylation. ACS Chem Biol 12: 1665-1673, 2017.*

Durocher et al., "Expression systems for therapeutic glycoprotein production", Current Opinion in Biotechnology, 2009, 20: 700-707.

Ehret er at., "Impact of cell culture media additives on IgG glycosylation produced in Chinese hamster ovary cells", Biotechnology and Bioengineering, Apr. 2019, 116: 816-830.

Van Berkel et al., "Rapid Production of Recombinant Human IgG With Improved ADCC Effector Function in a Transient Expression System", Biotechnology and Bioengineering, 2010, 105(2): 350-357.

Zhou et al., "Development of A Simple and Rapid Method for Producing Non-Fucosylated Oligomannose Containing Antibodies With Increased Effector Function", Biotechnology and Bioengineering, 2008, 99(3): 652-665.

* cited by examiner

*Primary Examiner* — Bridget E Bunner

(74) *Attorney, Agent, or Firm* — James S. Keddie; Bozicevic, Field & Francis LLP

(57) ABSTRACT

The present invention is directed to use of kifunensine for increasing sialylation of a glycosylated polypeptide, wherein a cell that produces the glycosylated polypeptide is contacted with kifunensine. Also provided are related methods for increasing sialylation of a glycosylated polypeptide and producing a glycosylated polypeptide, as well as glycosylated polypeptides and pharmaceutical compositions comprising the same, and their use in medicine.

17 Claims, 2 Drawing Sheets

Specification includes a Sequence Listing.

```
                         SEQUENCE LISTING

<160> NUMBER OF SEQ ID NOS: 4

<210> SEQ ID NO 1
<211> LENGTH: 456
<212> TYPE: PRT
<213> ORGANISM: Artificial Sequence
<220> FEATURE:
<223> OTHER INFORMATION: Golimumab Heavy Chain IgG1

<400> SEQUENCE: 1

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
        35                  40                  45

Ala Phe Met Ser Tyr Asp Gly Ser Asn Lys Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ala Ala Gly Gly Asn Tyr Tyr Tyr Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
```

-continued

```
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455


<210> SEQ ID NO 2
<211> LENGTH: 215
<212> TYPE: PRT
<213> ORGANISM: Artificial Sequence
<220> FEATURE:
<223> OTHER INFORMATION: Golimumab Light Chain

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
```

```
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 3
<211> LENGTH: 448
<212> TYPE: PRT
<213> ORGANISM: Artificial Sequence
<220> FEATURE:
<223> OTHER INFORMATION: Denosumab Heavy Chain IgG2

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Thr Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Gly Thr Thr Val Ile Met Ser Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
```

```
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Phe Arg Val Val
    290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 4
<211> LENGTH: 215
<212> TYPE: PRT
<213> ORGANISM: Artificial Sequence
<220> FEATURE:
<223> OTHER INFORMATION: Denosumab Light Chain (kappa)

<400> SEQUENCE: 4

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Gly Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Phe Tyr Cys Gln Gln Tyr Gly Ser Ser Pro
                85                  90                  95

Arg Thr Phe Gly Gln Gly Thr Lys Val Glu Ile Lys Arg Thr Val Ala
```

-continued

```
          100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

GLYCOSYLATED POLYPEPTIDES

CROSS-REFERENCE TO RELATED APPLICATIONS

This application is a § 371 national phase of International Application No. PCT/EP2020/085741, filed on Dec. 11, 2020, which claims the benefit of European Application No. 19215729.5, filed on Dec. 12, 2019, which applications are incorporated by reference herein.

The present invention relates to glycosylated polypeptides and production of the same.

The glycosylation profile of a polypeptide, such as a therapeutic polypeptide, is an important characteristic that can influence: biological activity through changes in half-life; affinity for an antigen or substrate by altering folding; and antibody-dependent cellular cytotoxicity (ADCC, one of the mechanisms responsible for the therapeutic effect of antibodies). The glycosylation profile of recombinant polypeptides is influenced by the cell line used for its production and the various cell culture parameters, including, for example, pH, temperature, cell culture media composition, and culture duration.

Modulation of polypeptide glycosylation is of particular relevance for marketed therapeutic polypeptides, since glycosylation levels (such as mannosylation and/or sialylation levels) can impact therapeutic utility and safety. Further, in the frame of biosimilar compounds, control of the glycosylation profile of a recombinant polypeptide is crucial, as the glycosylation profile of said recombinant polypeptide has to be comparable to that of the reference product. The enrichment of particular glycan structures is one of the challenges during process development.

Terminal sialyation of glycans is of particular importance for therapeutic polypeptides, with asialyted glycosylated polypeptides exhibiting reduced therapeutic efficacy owing to reduced half-life in vivo.

Sialylation has, to date, been manipulated mainly by way of: (i) non-selective cell culture additives; or (ii) transgenic cell lines with modulated expression of key enzymes involved in sialylation.

Non-selective cell culture additives include relevant transition metal cofactors. Said metal cofactors can modulate the glycosylation profile of polypeptides by regulating enzymes of the glycosylation pathway. For example, manganese has been shown to enhance sialylation of N-linked glycans in the presence of uridine and galactose. While the use of transition metals is well-established, their lack of specificity means that rigorous characterisation is required to identify the precise media composition necessary to achieve the desired level of each particular glycan structure without affecting other parameters, such as cell viability.

Engineered cells expressing altered levels of sialyl transferase enzymes (which transfer sialic acid onto polysaccharide chains, including those found on glycosylated polypeptides) have been used to affect the sialylation of resultant polypeptides. These cell lines require extensive, time consuming development and may only be useful in the production of a particular glycosylated polypeptide or class of glycosylated polypeptides.

Thus, despite the numerous methodological advances in the field in recent years, there remains a need for improved culture conditions and methods for the modulation of polypeptide glycosylation, in particular, sialylation.

The present invention overcomes one or more of the above mentioned problems.

The present inventors have found that kifunensine increases the sialyation of glycosylated polypeptides. The increase in sialylation was completely unexpected in view of kifunensine's mannosidase inhibitory activity as it is conventionally believed that mannosidase activity is essential for sialylation. Mannosidase processes glycans to remove mannose allowing for galactosylation; the substrate for terminal sialylation. In other words, sialylation relies on the very pathway that is inhibited by kifunensine and, thus in contrast to the inventors' findings, it would be expected that use of kifunensine would result in reduced sialylation.

In one aspect, the invention provides a use of kifunensine for increasing sialylation of a glycosylated polypeptide, wherein a cell that produces the glycosylated polypeptide is contacted with kifunensine.

In a related aspect, the present invention provides a method for increasing sialylation of a glycosylated polypeptide, the method comprising:

a. providing a cell that produces the glycosylated polypeptide; and
b. contacting the cell with kifunensine, thereby increasing sialylation of the glycosylated polypeptide produced by the cell.

In another aspect, the invention provides a method for producing a glycosylated polypeptide having increased sialylation, the method comprising:

a. providing a cell that produces the glycosylated polypeptide; and
b. contacting the cell with kifunensine, thereby producing the glycosylated polypeptide having increased sialylation.

Advantageously, the present inventors have found that both mannosylation and sialylation of glycosylated polypeptides can be readily manipulated with a single agent, kifunensine, without modifying for example, the cell line used.

The term "kifunensine" as used herein refers to (5R,6R,7S,8R,8aS)-6,7,8-trihydroxy-5-(hydroxymethyl)-1,5,6,7,8,8a-hexahydroimidazo[1,2-a]pyridine-2,3-dione as well as pharmacologically active salts, derivatives, or analogues thereof. Preferably, the term "kifunensine" refers to (5R,6R,7S,8R,8aS)-Hexahydro-6,7,8-trihydroxy-5-(hydroxymethyl)-imidazo[1,2-a]pyridine-2,3-dione only. Kifunensine has been assigned Chemical Abstracts Service registry number (CAS No.) 109944-15-2.

In one embodiment a "pharmacologically active salt, derivative, or analogue" of kifunensine is one that exhibits similar functional properties to kifunensine. Preferably, said pharmacologically active salt, derivative, or analogue inhibits mannosidase I. A pharmacologically active salt, derivative, or analogue of kifunensine may exhibit improved mannosidase I inhibitory activity when compared to kifunensine or may exhibit at least 50% (e.g. at least 60%, 70%, 80% or 90%) of the mannosidase I inhibitory activity of kifunensine.

Kifunensine is an alkaloid originally isolated from the actinobacterium, Kitasatosporia kifuense and is a well-established inhibitor of alpha-mannosidase I (mannosyl-oligosaccharide 1,2-alpha-mannosidase [EC 3.2.1.113]). This enzyme catalyses the hydrolysis of the terminal alpha-1,2-linked mannose residues from N-linked glycans. Kifunensine's inhibitory action on alpha-mannosidase I can therefore be used in the preparation of high mannose glycoproteins in cultured mammalian cells.

The term "glycosylated polypeptide" as used herein refers to a polypeptide conjugated to at least one polysaccharide (a "glycan"). The predominant carbohydrate moieties found on glycosylated polypeptides are fucose, galactose, glucose, mannose, N-acetylgalactosamine ("GalNAc"), N-acetylglucosamine ("GlcNAc"), xylose and sialic acid. The nature of glycans may impact the three-dimensional structure and the stability of the proteins to which they are conjugated. The glycan structures found in naturally occurring glycosylated polypeptides are divided into two main classes: "N-linked glycans" (the main form found in in eukaryotic cells) and "O-linked glycans". Polypeptides expressed in eukaryotic cells typically comprise N-glycans. The processing of the sugar groups for N-linked glycoproteins occurs in the lumen of the endoplasmic reticulum and continues in the Golgi apparatus. These N-linked glycans are conjugated to asparagine residues in the polypeptide primary structure, at sites containing the amino acid sequence asparagine-X-serine/threonine (where "X" is any amino acid residue except proline and aspartic acid). N-glycans differ with respect to the number of branches (also called "antennae") comprising sugars, as well as in the nature of said branch(es), which (in addition to the core structure) can include mannose, GlcNAc, galactose, GalNaC, fucose and/or sialic acid (including N-acetylneuraminic acid, the predominant sialic acid found in human cells), for instance. For a review of standard glycobiology nomenclature see Essentials of Glycobiology, 1999, Cold Spring Harbor Laboratory Press, ISBN-10: 0-87969-559-5, which is incorporated herein by reference.

A glycosylated polypeptide in accordance with the invention is preferably one conjugated to a glycan comprising a sialyl residue. Thus, in a preferred embodiment a glycosylated polypeptide is a sialylated polypeptide. In one embodiment, a glycosylated polypeptide of the invention may be one that is sialylated when expressed under non-recombinant conditions, e.g. endogenously in vivo.

The term "sialylation" as used herein refers to addition of sialic acid residues to a glycan structure found on a glycosylated polypeptide. Similarly "sialylation" may also refer to conjugation of a glycan comprising sialic acid to a polypeptide. Sialic acids are most often found at the terminal position of glycans. Sialylation can significantly influence the safety and efficacy profiles of these polypeptides. In particular, the in vivo half-life of some biopharmaceuticals correlates with the degree of polysaccharide sialylation. Furthermore, the sialylation pattern can be a very useful measure of product consistency during manufacturing. The two main types of sialyl residues found in biopharmaceuticals produced in mammalian expression systems are N-acetylneuraminic acid (NANA) and N-glycolylneuraminic acid (NGNA). These usually occur as terminal structures attached to galactose residues at the non-reducing termini of both N- and O-linked glycans.

A glycosylated polypeptide may be from any suitable source. For example, said polypeptide may be a eukaryotic or prokaryotic polypeptide. In one embodiment a glycosylated polypeptide of the invention is a eukaryotic polypeptide, preferably a mammalian glycosylated polypeptide, e.g. a human or murine glycosylated polypeptide. In a particularly preferred embodiment, a glycosylated polypeptide is a human glycosylated polypeptide.

In other embodiments, a glycosylated polypeptide may be a chimera comprising polypeptide sequences from a plurality of sources, e.g. comprising human and murine sequences.

In one embodiment, a glycosylated polypeptide is a recombinant glycosylated polypeptide, such as a recombinant antibody or antigen-binding portion thereof, preferably a recombinant antibody.

A glycosylated polypeptide may suitably be a therapeutic protein. Proteins with actual or potential therapeutic use are known to those skilled in the art. By way of non-limiting example, the glycosylated polypeptide may be an antibody or an antigen-binding portion of an antibody (such as a human antibody or antigen-binding portion thereof, a humanised antibody or antigen-binding portion thereof, a chimeric antibody or antigen-binding portion thereof, a bispecific antibody or antigen-binding portion thereof), a hormone (such as erythropoietin (EPO), parathyroid hormone, growth hormone, insulin or glucagon), an Fc-fusion polypeptide, an albumin fusion polypeptide (e.g. where a fusion partner is fused to albumin), an enzyme, or a cytokine.

In one embodiment, a glycosylated polypeptide is an Fc-fusion polypeptide. Fc-fusion polypeptides are known in the art and are described in Czajkowsky et al (2012), 4(10), 1015-1028, which is incorporated herein by reference. Fc-fusion polypeptides comprise (or consist of) an immunoglobulin Fc domain linked to a fusion partner. Said fusion partner may be a polypeptide (or peptide) of interest, such as a ligand, antigen, 'bait' (for identifying binding partners, e.g. in an array), extracellular binding domain or receptor, or a therapeutic polypeptide. Advantageously, the Fc domain is believed to increase the plasma half-life of the fusion partner and enables the Fc-fusion to interact with Fc-receptors (FcRs) found on immune cells; a feature that is particularly important for their use in oncological therapies and vaccines. By way of non-limiting example, the Fc-fusion polypeptide may be abatacept, aflibercept, alefacept, belatacept, etarnecept or rilonacept.

Preferably, a glycosylated polypeptide of the invention is an antibody or an antigen-binding portion thereof.

The term "antibody", and its plural form "antibodies", includes, inter alia, polyclonal antibodies, affinity-purified polyclonal antibodies, monoclonal antibodies, and antigen-binding portions/fragments, such as F(ab')2, Fab proteolytic fragments, and single chain variable region fragments (scFvs). Thus, in one embodiment an antibody herein is an antigen-binding portion of an antibody. Genetically engineered intact antibodies or fragments, such as chimeric antibodies, humanised antibodies, human or fully human antibodies, scFv and Fab fragments, as well as synthetic antigen-binding peptides and polypeptides, are also included.

The term "humanised" immunoglobulin (or "humanised antibody") refers to an immunoglobulin comprising a human framework region and one or more CDRs from a non-human (usually a mouse or rat) immunoglobulin. The non-human immunoglobulin providing the CDRs is called the "donor" and the human immunoglobulin providing the framework is called the "acceptor". Humanisation may be carried out by grafting non-human CDRs onto human framework and constant regions, or by incorporating the entire non-human variable domains onto human constant regions (chimerisation). Constant regions need not be present, but if they are, they must be substantially identical to human immunoglobulin constant regions, i.e., at least about 85-90%, preferably about 95% or more identical. Hence, all parts of a humanised immunoglobulin, except possibly the CDRs and a few residues in the heavy chain constant region if modulation of the effector functions is needed, are substantially identical to corresponding parts of natural human immunoglobulin sequences. Through humanising antibodies, biological half-life may be increased, and the potential for adverse immune reactions upon administration to humans is reduced.

The term "fully human" immunoglobulin (or "fully-human" antibody) refers to an immunoglobulin comprising both a human framework region and human CDRs. Constant regions need not be present, but if they are, they must be substantially identical to human immunoglobulin constant regions, i.e., at least about 85-90%, preferably about 95% or more identical. Hence, all parts of a fully human immunoglobulin, except possibly a few residues in the heavy chain constant region if modulation of the effector functions or pharmacokinetic properties are needed, are substantially identical to corresponding parts of natural human immunoglobulin sequences. In some instances, amino acid mutations may be introduced within the CDRs, the framework regions or the constant region, in order to improve the binding affinity and/or to reduce the immunogenicity and/or to improve the biochemical/biophysical properties of the antibody.

The term "recombinant antibody" (or "recombinant immunoglobulin") means an antibody produced by recombinant techniques. Recombinant host cells for the production of antibodies include recombinant prokaryotic and eukaryotic cells; preferably mammalian host cells, such as Chinese Hamster Ovary (CHO) cells (including CHO—S cells or CHO-k1 cells). The term "recombinant antibody" therefore refers to an antibody produced in recombinant (e.g. mammalian) cells. Because of the relevance of recombinant DNA techniques in the generation of antibodies, one needs not be confined to the sequences of amino acids found in natural antibodies; antibodies can be redesigned to obtain desired characteristics. The possible variations are many and range from the changing of just one or a few amino acids to the complete redesign of, for example, the variable domain or constant region. Changes in the constant region will, in general, be made in order to improve, reduce or alter characteristics, such as complement fixation (e.g. complement dependent cytotoxicity, CDC), interaction with Fc receptors, and other effector functions (e.g. antibody dependent cellular cytotoxicity, ADCC), pharmacokinetic properties (e.g. binding to the neonatal Fc receptor; FcRn). Changes in the variable domain will be made in order to improve the antigen binding characteristics. In addition to antibodies, immunoglobulins may exist in a variety of other forms including, for example, single-chain or Fv, Fab, and (Fab')2, as well as diabodies, linear antibodies, multivalent or multispecific hybrid antibodies.

The term "antibody portion" or "antibody fragment" refers to a fragment of an intact or a full-length chain or antibody, usually the binding or variable region. Said portions, or fragments, should maintain at least one activity of the intact chain/antibody, i.e. they are "functional portions" or "functional fragments". Should they maintain at least one activity, they preferably maintain the target binding property. Examples of antibody portions (or antibody fragments) include, but are not limited to, "single-chain Fv", "single-chain antibodies", "Fv" or "scFv". These terms refer to antibody fragments that comprise the variable domains from both the heavy and light chains, but lack the constant regions, all within a single polypeptide chain. Generally, a single-chain antibody further comprises a polypeptide linker between the VH and VL domains which enables it to form the desired structure that would allow for antigen binding. In specific embodiments, single-chain antibodies can also be bi-specific and/or humanised. A "Fab fragment" is comprised of one light chain and the variable and CH1 domains of one heavy chain. The heavy chain of a Fab molecule cannot form a disulfide bond with another heavy chain molecule. A "Fab' fragment" that contains one light chain and one heavy chain and contains more of the constant region, between the CH1 and CH2 domains, such that an interchain disulfide bond can be formed between two heavy chains is called a F(ab')2 molecule. A "F(ab')2" contains two light chains and two heavy chains containing a portion of the constant region between the CH1 and CH2 domains, such that an interchain disulfide bond is formed between two heavy chains.

A polypeptide of the invention may be a full-length antibody or a fragment thereof. Preferably, a polypeptide of the invention is a full-length antibody comprising (or consisting of) each of the antibody regions/domains present in a full-length antibody (e.g. obtainable from a mammal, such as a human or mouse). Said antibody may comprise (or consist of) two heavy chains, and two light chains, wherein the heavy chains each comprise (or consist of) a VH domain, a CH1 domain, a CH2 domain, and a CH3 domain and the light chains each comprise (or consist of) a CL domain and a VL domain.

In a preferred embodiment, an antibody according to the present invention is a monoclonal antibody (or antigen-binding portion thereof).

In one embodiment, an antibody is an antigen-binding portion comprising or consisting of a Fab, $F(ab)_2$ or single-chain variable fragment (scFv).

In accordance with the present invention, the antibody or antigen-binding portion thereof may belong to any Ig type, for example, IgG1, IgG2, IgG3 or IgG4.

In some embodiments, the antibody or antigen-binding portion thereof may be adalimumab, abciximab, alemtuzumab, atezolizumab, avelumab, basiliximab, bevacizumab, brodalumab, certolizumab, cetuximab, daratumumab, daclizumab, denosumab, dupilumab, durvalumab, eculizumab, efalizumab, gemtuzumab, golimumab, guselkumab, ibritumomab, infliximab, ixekizumab, muromonab-CD3, natalizumab, nivolumab, omalizumab, palivizumab, panitumumab, pembrolizumab, ranibizumab, risankizumab, rituximab, secukinumab, tildrakizumab, tocilizumab, tositumomab, trastuzumab, ustekinumab, or vedolizumab.

In some embodiments where the glycosylated polypeptide is an antibody, the glycosylated polypeptide is an IgG1 antibody or an IgG2 antibody. Advantageously, the present inventors have shown that sialylation of both IgG1 and IgG2 antibodies are increased by contacting cells producing said antibodies with kifunensine.

An antibody or antigen-binding portion thereof of the invention may bind to one or more antigens, preferably simultaneously. For example, an antibody may bind to two antigens (a bi-specific antibody) or three antigens (a tri-specific antibody).

In one embodiment the antibody or antigen-binding portion thereof binds to an antigen having a known or potential therapeutic significance, such as a disease-related antigen. By way of non-limiting example, the antibody or antigen-binding portion thereof may bind an antigen that is involved in the initiation, development, progression or worsening of a disease for example, cancer, inflammatory disease, autoimmune disease, cardiovascular disease or ophthalmologic disease. In one embodiment the antibody or antigen-binding portion thereof is one that binds to a cytokine or receptor thereof, for example an antibody or antigen-binding portion thereof that binds to one or more of interleukin-6 (IL-6), an IL-6 receptor (e.g. tocilizumab described in WO 2019/043096), tumour necrosis factor alpha (TNFα), a TNFα receptor, interleukin 12 (IL-12), an IL-12 receptor, interleukin 23 (IL-23), an IL-23 receptor, interleukin 17 (IL-17), an IL-17 receptor, interleukin 17A (IL-17A) or an IL-17A receptor.

In some embodiments the antibody or antigen-binding portion thereof is an anti-IL-12 and/or anti-IL-23 antibody.

For example, the anti-IL-12 and/or anti-IL-23 antibody or antigen-binding portion thereof may be ustekinumab, guselkumab, tildrakizumab or risankizumab. In a preferred embodiment, the anti-IL-12 and anti-IL-23 antibody, ustekinumab.

In some embodiments the antibody or antigen-binding portion thereof is an anti-IL-17 antibody or an anti-IL-17 receptor antibody. For example, the anti-IL-17 antibody may be secukinumab or ixekizumab and the anti-IL-17 receptor antibody may be brodalumab.

In some embodiments the antibody or antigen-binding portion thereof is an anti-TNFα antibody. For example, the anti-TNFα antibody or antigen-binding portion thereof may be golimumab, adalimumab, etanercept or certolizumab. In a preferred embodiment, the anti-TNFα antibody or antigen-binding portion thereof is golimumab.

In some embodiments the anti-TNFα antibody or antigen-binding portion thereof comprises a heavy chain having at least 70% sequence identity to SEQ ID NO: 1. For example, the anti-TNFα antibody or antigen-binding portion thereof may comprise a heavy chain having at least 80%, 90%, 95%, 96%, 97%, 98% or 99% sequence identity to SEQ ID NO: 1. Preferably, the anti-TNFα antibody or antigen-binding portion thereof comprises a heavy chain that comprises (more preferably consists of) SEQ ID NO: 1.

In some embodiments the anti-TNFα antibody or antigen-binding portion thereof comprises a light chain having at least 70% sequence identity to SEQ ID NO: 2. For example, the anti-TNFα antibody or antigen-binding portion thereof may comprise a light chain having at least 80%, 90%, 95%, 96%, 97%, 98% or 99% sequence identity to SEQ ID NO: 2. Preferably, the anti-TNFα antibody or antigen-binding portion thereof comprises a light chain that comprises (more preferably consists of) SEQ ID NO: 2.

In some embodiments the anti-TNFα antibody or antigen-binding portion thereof comprises a heavy chain having at least 70% sequence identity to SEQ ID NO: 1 and a light chain having at least 70% sequence identity to SEQ ID NO: 2. Preferably, the anti-TNFα antibody or antigen-binding portion thereof comprises a heavy chain having at least 80%, 90%, 95%, 96%, 97%, 98% or 99% sequence identity to SEQ ID NO: 1 and a light chain having at least 80%, 90%, 95%, 96%, 97%, 98% or 99% sequence identity to SEQ ID NO: 2. Even more preferably, the anti-TNFα antibody or antigen-binding portion thereof comprises a heavy chain that comprises (more preferably consists of) SEQ ID NO: 1 and a light chain that comprises (more preferably consists of) SEQ ID NO: 2.

In some embodiments the anti-TNFα antibody or antigen-binding portion thereof comprises a heavy chain variable region ($V_H$) having at least 70% identity to the corresponding $V_H$ sequence of SEQ ID NO: 1. Preferably, the anti-TNFα antibody or antigen-binding portion thereof comprises a $V_H$ having at least 80%, 90%, 95%, 96%, 97%, 98% or 99% sequence identity to the corresponding $V_H$ sequence of SEQ ID NO: 1. Even more preferably, the anti-TNFα antibody or antigen-binding portion thereof comprises a $V_H$ that comprises (more preferably consists of) the corresponding $V_H$ sequence of SEQ ID NO: 1.

In some embodiments the anti-TNFα antibody or antigen-binding portion thereof comprises a light chain variable region ($V_L$) having at least 70% sequence identity to the corresponding $V_L$ sequence of SEQ ID NO: 2. Preferably, the anti-TNFα antibody or antigen-binding portion thereof comprises a $V_L$ having at least 80%, 90%, 95%, 96%, 97%, 98% or 99% sequence identity to the corresponding $V_L$ sequence of SEQ ID NO: 2. Even more preferably, the anti-TNFα antibody or antigen-binding portion thereof comprises a $V_L$ that comprises (more preferably consists of) the corresponding $V_L$ sequence of SEQ ID NO: 1.

In some embodiments the anti-TNFα antibody or antigen-binding portion thereof comprises a heavy chain CDR1, heavy chain CDR2 and heavy chain CDR3 sequence having at least 70% sequence identity to the corresponding heavy chain CDR1, heavy chain CDR2 and heavy chain CDR3 sequence of SEQ ID NO: 1. Preferably, the anti-TNFα antibody or antigen-binding portion thereof comprises a heavy chain CDR1, heavy chain CDR2 and heavy chain CDR3 sequence having at least sequence 80%, 90%, 95%, 96%, 97%, 98% or 99% identity to the corresponding heavy chain CDR1, heavy chain CDR2 and heavy chain CDR3 sequence of SEQ ID NO: 1. Even more preferably, the anti-TNFα antibody or antigen-binding portion thereof comprises a heavy chain CDR1, heavy chain CDR2 and heavy chain CDR3 that comprises (more preferably consists of) the corresponding heavy chain CDR1, heavy chain CDR2 and heavy chain CDR3 sequence of SEQ ID NO: 1.

In some embodiments the anti-TNFα antibody or antigen-binding portion thereof comprises a light chain CDR1, light chain CDR2 and light chain CDR3 sequence having at least 70% sequence identity to the corresponding light chain CDR1, light chain CDR2 and light chain CDR3 sequence defined by SEQ ID NO: 2. Preferably, the anti-TNFα antibody or antigen-binding portion thereof comprises a light chain CDR1, light chain CDR2 and light chain CDR3 sequence having at least 80%, 90%, 95%, 96%, 97%, 98% or 99% sequence identity to the corresponding light chain CDR1, light chain CDR2 and light chain CDR3 sequence of SEQ ID NO: 2. Even more preferably, the anti-TNFα antibody or antigen-binding portion thereof comprises a light chain CDR1, light chain CDR2 and light chain CDR3 that comprises (more preferably consists of) the corresponding light chain CDR1, light chain CDR2 and light chain CDR3 sequence of SEQ ID NO: 2.

In some embodiments the anti-TNFα antibody or antigen-binding portion thereof comprises a heavy chain CDR1, heavy chain CDR2 and heavy chain CDR3 sequence that consists of the corresponding heavy chain CDR1, heavy chain CDR2 and heavy chain CDR3 sequence of SEQ ID NO: 1 and a light chain CDR1, light chain CDR2 and light chain CDR3 that consists of the corresponding light chain CDR1, light chain CDR2 and light chain CDR3 sequence of SEQ ID NO: 2.

In other embodiments, an antibody or antigen-binding portion thereof is one that binds to receptor activator of nuclear factor-kappa B ligand (RANKL), receptor tyrosine-protein kinase erbB-2 (HER2), receptor tyrosine-protein kinase erbB-3 (HER3), vascular endothelial growth factor (VEGF), VEGF-A, B-lymphocyte antigen CD20 (CD20), programmed cell death protein 1 (PD-1), or programmed death-ligand 1 (PD-L1).

In some embodiments the antibody or antigen-binding portion thereof is an anti-RANKL antibody or antigen-binding portion thereof. An exemplary anti-RANKL antibody or antigen-binding portion thereof is denosumab.

In some embodiments the anti-RANKL antibody or antigen-binding portion thereof comprises a heavy chain having at least 70% sequence identity to SEQ ID NO: 3. For example, the anti-RANKL antibody or antigen-binding portion thereof may comprise a heavy chain having at least 80%, 90%, 95%, 96%, 97%, 98% or 99% sequence identity to SEQ ID NO: 3.

Preferably, the anti-RANKL antibody or antigen-binding portion thereof comprises a heavy chain that comprises (more preferably consists of) SEQ ID NO: 3.

In some embodiments the anti-RANKL antibody or antigen-binding portion thereof comprises a light chain having at least 70% sequence identity to SEQ ID NO: 4. For example, the anti-RANKL antibody or antigen-binding portion thereof may comprise a light chain having at least 80%, 90%, 95%, 96%, 97%, 98% or 99% sequence identity to SEQ ID NO: 4. Preferably, the anti-RANKL antibody or antigen-binding portion thereof comprises a light chain that comprises (more preferably consists of) SEQ ID NO: 4.

In some embodiments the anti-RANKL antibody or antigen-binding portion thereof comprises a heavy chain having at least 70% sequence identity to SEQ ID NO: 3 and a light chain having at least 70% sequence identity to SEQ ID NO: 4. Preferably, the anti-RANKL antibody or antigen-binding portion thereof comprises a heavy chain having at least 80%, 90%, 95%, 96%, 97%, 98% or 99% sequence identity to SEQ ID NO: 3 and a light chain having at least 80%, 90%, 95%, 96%, 97%, 98% or 99% sequence identity to SEQ ID NO: 4. Even more preferably, the anti-RANKL antibody or antigen-binding portion thereof comprises a heavy chain that comprises (more preferably consists of) SEQ ID NO: 3 and a light chain that comprises (more preferably consists of) SEQ ID NO: 4.

In some embodiments the anti-RANKL antibody or antigen-binding portion thereof comprises a heavy chain variable region ($V_H$) having at least 70% identity to the corresponding $V_H$ sequence of SEQ ID NO: 3. Preferably, the anti-RANKL antibody or antigen-binding portion thereof comprises a $V_H$ having at least 80%, 90%, 95%, 96%, 97%, 98% or 99% sequence identity to the corresponding $V_H$ sequence of SEQ ID NO: 3. Even more preferably, the anti-RANKL antibody or antigen-binding portion thereof comprises a $V_H$ that comprises (more preferably consists of) the corresponding $V_H$ sequence of SEQ ID NO: 3.

In some embodiments the anti-RANKL antibody or antigen-binding portion thereof comprises a light chain variable region ($V_L$) having at least 70% sequence identity to the corresponding $V_L$ sequence of SEQ ID NO: 4. Preferably, the anti-RANKL antibody or antigen-binding portion thereof comprises a $V_L$ having at least 80%, 90%, 95%, 96%, 97%, 98% or 99% sequence identity to the corresponding $V_L$ sequence of SEQ ID NO: 4. Even more preferably, the anti-RANKL antibody or antigen-binding portion thereof comprises a $V_L$ that comprises (more preferably consists of) the corresponding $V_L$ sequence of SEQ ID NO: 4.

In some embodiments the anti-RANKL antibody or antigen-binding portion thereof comprises a heavy chain CDR1, heavy chain CDR2 and heavy chain CDR3 sequence having at least 70% sequence identity to the corresponding heavy chain CDR1, heavy chain CDR2 and heavy chain CDR3 sequence of SEQ ID NO: 3. Preferably, the anti-RANKL antibody or antigen-binding portion thereof comprises a heavy chain CDR1, heavy chain CDR2 and heavy chain CDR3 sequence having at least sequence 80%, 90%, 95%, 96%, 97%, 98% or 99% identity to the corresponding heavy chain CDR1, heavy chain CDR2 and heavy chain CDR3 sequence of SEQ ID NO: 3. Even more preferably, the anti-RANKL antibody or antigen-binding portion thereof comprises a heavy chain CDR1, heavy chain CDR2 and heavy chain CDR3 that comprises (more preferably consists of) the corresponding heavy chain CDR1, heavy chain CDR2 and heavy chain CDR3 sequence of SEQ ID NO: 3.

In some embodiments the anti-RANKL antibody or antigen-binding portion thereof comprises a light chain CDR1, light chain CDR2 and light chain CDR3 sequence having at least 70% sequence identity to the corresponding light chain CDR1, light chain CDR2 and light chain CDR3 sequence defined by SEQ ID NO: 4. Preferably, the anti-RANKL antibody or antigen-binding portion thereof comprises a light chain CDR1, light chain CDR2 and light chain CDR3 sequence having at least 80%, 90%, 95%, 96%, 97%, 98% or 99% sequence identity to the corresponding light chain CDR1, light chain CDR2 and light chain CDR3 sequence of SEQ ID NO: 4. Even more preferably, the anti-RANKL antibody or antigen-binding portion thereof comprises a light chain CDR1, light chain CDR2 and light chain CDR3 that comprises (more preferably consists of) the corresponding light chain CDR1, light chain CDR2 and light chain CDR3 sequence of SEQ ID NO: 4.

In some embodiments the anti-RANKL antibody or antigen-binding portion thereof comprises a heavy chain CDR1, heavy chain CDR2 and heavy chain CDR3 sequence that consists of the corresponding heavy chain CDR1, heavy chain CDR2 and heavy chain CDR3 sequence of SEQ ID NO: 3 and a light chain CDR1, light chain CDR2 and light chain CDR3 that consists of the corresponding light chain CDR1, light chain CDR2 and light chain CDR3 sequence of SEQ ID NO: 4.

The $V_H$ or $V_L$ typically contains three CDRs and four framework regions (FRs), arranged from amino-terminus to carboxyl-terminus in the following order: FR1, CDR1, FR2, CDR2, FR3, CDR3, FR4. The amino acids that make up the CDRs and the FRs (and thus the variable regions), respectively, can be readily identified for any given heavy or light chain sequence by one of ordinary skill in the art, since they have been defined in various different ways (see, "Sequences of Proteins of Immunological Interest," Kabat, E., et al., U.S. Department of Health and Human Services, (1983); and Chothia and Lesk, J. Mol. Biol., 196:901-917 (1987)).

In embodiments where the glycosylated polypeptide is a hormone, the hormone may be any hormone with known or potential therapeutic applications. In some embodiments, the hormone is a human hormone. In some embodiments the hormone is erythropoietin (EPO), parathyroid hormone, growth hormone, insulin, glucagon, follicle stimulating hormone, luteinizing hormone or choriogonadotropin. In one embodiment, the glycosylated polypeptide is a hormone which regulates erythropoiesis. Preferably the hormone is EPO.

In embodiments where the glycosylated polypeptide is a cytokine, the cytokine may be any cytokine with known or potential therapeutic applications. In some embodiments the cytokine is a human cytokine. In one embodiment the cytokine is an interferon (IFN), for example, IFN alpha 2a, IFN alpha 2b, IFN beta 1a, IFN beta 1b, IFN gamma 1b.

In one embodiment a glycosylated polypeptide comprises at least one N-linked glycan. The N-linked glycan may be at least mono-antennary, bi-antennary, tri-antennary or tetra-antennary. In one embodiment, an N-linked glycan is a bi-antennary glycan.

In embodiments where the glycosylated polypeptide of the invention is an antibody or antigen-binding portion thereof (preferably an antibody), the antibody or antigen-binding portion thereof (preferably antibody) may comprise at least one N-linked glycan conjugated to the Fc portion of the antibody and/or a variable region thereof (e.g. a heavy-chain variable region and/or a light-chain variable region). Preferably, the antibody comprises at least one N-linked glycan conjugated to the Fc portion of the antibody.

Contacting a cell that produces a glycosylated polypeptide with kifunensine increases sialylation of said polypeptide. Thus, by carrying out a method or use of the invention the resultant glycosylated polypeptide exhibits increased sialylation.

The term "increased sialylation" encompasses an increase in the number of sialic acid groups conjugated to each polypeptide molecule and/or to an increase in the number of polypeptide molecules (e.g. produced in the method/use of the invention) that have sialic acid conjugated thereto. Preferably, the term "increased sialylation" encompasses an increase in the number of sialic acid groups conjugated to each polypeptide molecule and to an increase in the number of polypeptide molecules (e.g. produced in the method/use of the invention) that have sialic acid conjugated thereto. The sialic acid is a component of a glycan conjugated to a glycosylated polypeptide. The number of sialic acid groups conjugated to each polypeptide molecule and/or to the number of polypeptide molecules that have sialic acid conjugated thereto may be referred to herein as the "sialylation level".

Sialylation is increased when compared to the sialylation of the same glycosylated polypeptide produced under the same conditions (e.g. using the same cell line) but wherein the cell has not been contacted with kifunensine. Thus, to determine when sialylation is increased, the skilled person can compare the sialylation level of a polypeptide produced in accordance with a method or use of the invention with the same glycosylated polypeptide produced under the same conditions (e.g. using the same cell line) but wherein the cell has not been contacted with kifunensine.

A sialylation level may be conveniently expressed as a % sialylation level. In one embodiment, sialylation is increased by at least 0.2% (preferably 0.5%) when compared to the sialylation of the same glycosylated polypeptide produced under the same conditions (e.g. using the same cell line) but wherein the cell has not been contacted with kifunensine. In one embodiment sialylation is increased by at least 1% (preferably 1.5%) when compared to the sialylation of the same glycosylated polypeptide produced under the same conditions (e.g. using the same cell line) but wherein the cell has not been contacted with kifunensine. Preferably sialylation is increased by at least 2% when compared to the sialylation of the same glycosylated polypeptide produced under the same conditions (e.g. using the same cell line) but wherein the cell has not been contacted with kifunensine.

In one embodiment the increase in sialylation is statistically-significant.

In one embodiment a glycosylated polypeptide is an antibody having a glycan conjugated to the Fc portion thereof. Preferably, sialylation of an Fc portion of an antibody is increased and/or the number of antibodies having sialylation at said Fc portion is increased.

In some embodiments, a method or use of the invention may comprise a further step of analysing the glycosylation (preferably sialylation) of the glycosylated polypeptide. Methods for measuring/characterising glycosylation (and in particular sialylation levels) are well-known to the skilled person. Glycan analysis typically involves releasing glycans from the glycosylated polypeptide (for example, enzymatically), separating the individual glycans using liquid chromatography and detecting their presence or absence and/or composition. In order to detect glycans, they are typically labelled with fluorescent tags prior to analysis, for example, 2-aminobenzamide (2-AB) or 2-aminobenzoic acid (2-AA). In one embodiment, glycosylation/sialylation levels are determined by liquid chromatography and fluorescence detection. Preferably, the liquid chromatography is a hydrophilic interaction chromatography (HILIC).

Mass spectrometry may also be used to analyse glycosylation/sialylation levels. Mass spectrometry may be performed directly on a glycosylated polypeptide, or glycans may be released (for example, enzymatically) and isolated from the polypeptide and their structure separately analysed. Isolated glycans are typically analysed by liquid chromatography-mass spectrometry methods, such as HILIC-mass spectrometry or matrix assisted laser desorption ionisation (MALDI)-mass spectrometry. In one embodiment, glycosylation/sialylation levels are determined by HILIC-mass spectrometry. The mass spectrometry may be a matrix-assisted laser desorption/ionization time-of-flight (MALDI-TOF) mass spectrometry. In some embodiments, glycosylation/sialylation levels are analysed by mass spectrometry without a preceding chromatography step.

The methods and uses of the invention comprise contacting a cell with kifunensine. The cell is suitably part of a cell culture. The cell may be contacted in any manner suitable so long as the sialylation of a glycosylated polypeptide produced by said cell is increased.

Suitable conditions (such as time) can be determined by the skilled person, for example optimal conditions can be determined empirically by measuring and comparing sialylation levels under different conditions. In one embodiment, a cell may be contacted with kifunensine for at least 2, 5, 10, 15, 20, 25, 30, 35, 40, 45, 50, 55, 60, 65 or 70 hours. In other embodiments, a cell may be contacted with kifunensine for at least 5 days. Preferably, a cell may be contacted for at least 6, 7, 8, 9, 10, 11, 12, 13, 14, 15, 16, 17, 18, 19, 20, 21, 22, 23, 24 or 25 days. Even more preferably a cell may be contacted with kifunensine for at least 15 days. In one embodiment the cell is contacted with kifunensine for 20 days.

In some embodiments, a cell is contacted with kifunensine at a concentration that substantially inhibits mannosidase I activity. The term "substantially" as used in this context means that the mannosidase I activity of the cell is inhibited by at least 50%, 60%, 70%, 80%, 90%, or is completely inhibited when compared to the mannosidase I activity of an identical cell that has not been contacted with kifunensine. Means of determining mannosidase I activity are known in the art.

In some embodiments, a cell is contacted with kifunensine at a concentration that does not substantially inhibit mannosidase I activity. The expression "does not substantially inhibit" as used in this context means that a cell contacted with kifunensine has at least 80% of the mannosidase I activity of an identical cell that has not been contacted with kifunensine. Preferably a cell contacted with kifunensine has at least 90% (e.g. at least 95%, 96%, 97%, 98%, or 99%) of the mannosidase I activity of an identical cell that has not been contacted with kifunensine.

In one embodiment, a cell that produces a glycosylated polypeptide may be contacted with a solution comprising kifunensine. The solution is preferably a culture medium. In other words, kifunensine may be present in a culture medium used to culture a cell. The term "culture medium" is intended to embrace any medium suitable for maintaining viability, and preferably further promoting growth and division, of a cell. Typical basal culture media contains essential ingredients useful for cell metabolism, for instance, amino acids, lipids, carbon source, vitamins and mineral salts. DMEM (Dulbeccos' Modified Eagles Medium), RPMI (Roswell Park Memorial Institute Medium) or medium F12 (Ham's F12 medium) are examples of commercially available culture media. Alternatively, the culture medium may be a "chemically defined medium" or "chemically defined culture medium", in which all of the components can be described in terms of the chemical formulas and are present in known concentrations. The chemically defined medium may be a proprietary medium, fully developed in-house, or commercially available. The culture medium can be free of proteins and/or free of serum, and can be supplemented by any additional compound(s) such as amino acids, salts, sugars, vitamins, hormones or growth factors, depending on the needs of the cells in culture.

In one embodiment, a cell is contacted with a solution comprising less than 1 μM kifunensine. In one embodiment, a cell is contacted with a solution comprising kifunensine at a concentration of 750 nM or less, 500 nM or less, 250 nM or less or 150 nM or less.

In one embodiment, a cell is contacted with a solution comprising kifunensine at a concentration of at least 25 nM, 30 nM, 40 nM, 50 nM, 60 nM or 70 nM.

In one embodiment, a cell is contacted with a solution comprising kifunensine at a concentration of 25-950 nM, such as 30-750 nM, or 30-250 nM. In one embodiment a cell is contacted with a solution comprising kifunensine at a concentration of 30-150 nM. Preferably the cell is contacted with a solution comprising kifunensine at a concentration of 35-75 nM, more preferably 40-65 nM or 40-60 nM, or even more preferably about 50 nM.

In one embodiment, a cell is contacted with kifunensine at a concentration that has no significant effect on cell viability. The term "cell viability" may refer to the ratio between the total number of viable cells and the number of cells in culture.

A cell may be contacted with kifunensine at any time during culture of the cell. In one embodiment the cell is contacted with kifunensine prior to the production of the glycosylated polypeptide. By way of non-limiting example, the cell may be contacted with kifunensine immediately upon being inoculated into a culture vessel. In some embodiments, kifunensine will be present in culture media to which cells are added. Contacting prior to production may be particularly advantageous when the present invention employs the use of an inducible expression system for production of the glycosylated polypeptide.

In some embodiments kifunensine is added to culture media in which cells are present (e.g. in which cells are growing). In one embodiment a cell culture will be contacted with kifunensine once a certain cell density is reached. The term "cell density" refers to the number of cells in a given volume of culture medium. In some embodiments a cell culture is contacted with kifunensine when the cell density is about 1 million viable cells (vc)/ml or more, for example about 2 million, about 3 million, about 4 million vc/ml or about 5 million vc/ml. Preferably, the cell culture is contacted with kifunensine when the cell density is about 2.5 to 5 million vc/ml. Even more preferably, the cell culture is contacted with kifunensine when the cell density is about 3 to 4 million vc/ml.

In another embodiment a cell is contacted with kifunensine during production of the glycosylated polypeptide (e.g. once expression of the glycosylated polypeptide has commenced).

In one embodiment, a cell is cultured in a fed-batch culture system. The term "fed-batch culture" is intended to embrace a method of growing cells, where there is a bolus or continuous feed media supplementation to replenish the nutrients which are consumed. This cell culture technique has the potential to obtain high cell densities in the order of greater than $10\times10^6$ to $30\times10^6$ cells/ml, depending on the media formulation, cell line, and other cell growth conditions. A biphasic culture condition can be created and sustained by a variety of feed strategies and media formulations that are well-known to the skilled person.

In one embodiment wherein the cell is cultured in a fed-batch culture system, the cell is contacted with feed media comprising kifunensine. In another embodiment, the cell is contacted a plurality of times throughout the production phase with feed media comprising kifunensine. In some embodiments the cell is contacted with kifunensine immediately upon being inoculated into a production bioreactor. The term "inoculate" is intended to encompass the process of introducing a cell into a culture vessel, for example production bioreactors which are commonly used to produce recombinant glycosylated polypeptides.

In another embodiment a cell is cultured in a perfusion culture system. Perfusion culture is one in which the cell culture receives fresh perfusion feed medium while simultaneously removing spent medium. Perfusion can be continuous, step-wise, intermittent, or a combination thereof. Perfusion rates can be less than a working volume to many working volumes per day. Preferably the cells are retained in the culture and the spent medium that is removed is substantially free of cells or has significantly fewer cells than the culture.

Perfusion can be accomplished by a number of cell retention techniques including centrifugation, sedimentation, or filtration (see for example Voisard et al (2003), Biotechnol Bioteng, 30; 82(7), 751-65). In accordance with the present invention, the glycosylated polypeptide may be secreted by the cell into the medium (e.g. growth medium) and extracted from the supernatant throughout the culture period following application of one or more of the aforementioned cell retention techniques. Alternatively, the secreted polypeptide may also be retained during the culture period and subsequently extracted at the end of the culture.

In one embodiment wherein the cell is cultured in a perfusion culture system, the cell is contacted continuously throughout the production phase with perfusion feed medium comprising kifunensine.

Any cell capable of producing a glycosylated polypeptide comprising sialylation may be employed in the present invention. The cell may be a cell line, e.g. an immortalised cell line. The cell may be referred to herein as a "host cell". It will be understood by the skilled person that a cell of the invention expresses a polypeptide, which is then glycosylated by the cell.

A cell for use in the invention may be a eukaryotic cell. Suitable eukaryotic cells may include mammalian cells (e.g. HEK293 cells or HeLa cells), yeast cells (e.g. *Saccharomyces cerevisiae* or *Pichia pastoris*) or insect cells (e.g. baculovirus-infected insect cells).

Cells for use in the invention may be selected from Chinese hamster ovary (CHO) cells, myeloma cell lines (for example, NSO, Sp2/0), HeLa cells, HEK 293 cells, Cos cells, 3T3 cells, PER.C6 cells, S2 cells, Sf9 cells, Sf21 cells, *E. coli* cells, *S. cerevisiae* cells, and *Pichia pastoris* cells. The skilled person can select a cell type that is most appropriate for the production of the glycosylated polypeptide of interest. Chimeric or hybrid cells may also be utilised in accordance with the invention.

In one embodiment, the cell is a human cell, a non-human primate cell or a rodent cell, for example a murine cell, a hamster cell or a human cell. Preferably, a cell is a Sp2/0 or CHO cell.

A cell for use in the invention comprises a nucleic acid that encodes a polypeptide of the invention. A nucleic acid of the invention may be comprised in a vector for expression in a host cell. Thus, the invention also provides vectors and host cells comprising a nucleic acid of the invention. The vectors may comprise a promoter operably linked to a nucleic acid of the invention and may further comprise a terminator. In some embodiments the vector comprising a nucleic acid that encodes a polypeptide of the invention further comprises a nucleic acid encoding a selectable marker. The term "selectable marker" is intended to encompass nucleic acid sequences that when introduced into a cell confer a trait suitable for selection of the resulting cell. Nucleic acids encoding selectable markers are well known to the skilled person, for example, the gene encoding glutamine synthetase, dihydrofolate reductase (DHFR) or puromycin N-acetyltransferase. Alternatively, the selectable marker may encode a puro-DHFR fusion protein as described in WO2008/148881. Where a polypeptide of the invention comprises two or more polypeptide chains (e.g. antibody heavy and light chains) the invention may employ the use of two or more vectors.

The nucleic acid molecules of the invention may be made using any suitable process known in the art. In one embodiment, the nucleic acid molecules may be made using chemical synthesis techniques. Alternatively, the nucleic acid molecules of the invention may be made using molecular biology techniques.

The DNA construct of the present invention may be designed in silico, and then synthesised by conventional DNA synthesis techniques.

The above-mentioned nucleic acid sequence information is optionally modified for codon-biasing according to the ultimate host cell expression system that is to be employed.

The terms "nucleotide sequence" and "nucleic acid" are used synonymously herein. Preferably the nucleotide sequence is a DNA sequence.

A glycosylated polypeptide produced according to the invention may be isolated. Methods of isolating glycosylated polypeptides produced by cells are known in the art. Thus, in one embodiment, a use or method may comprise a step of isolating the glycosylated polypeptide.

An isolated polypeptide may be free from alternative polypeptides or cellular matter, e.g. substantially free from any alternative polypeptides or cellular matter. In other words, a fusion polypeptide may be considered "isolated" when the polypeptide of the invention constitutes at least 90% of the total polypeptides present, preferably when the polypeptide of the invention constitutes at least 95%, 98% or 99% (more preferably at least 99.9%) of the total polypeptides present. Isolating can be achieved using any suitable methods known in the art such as any suitable purification methods, e.g. chromatographic methods. Suitable methods may include affinity chromatography, ion exchange (e.g. cation or anion exchange) chromatography and immunoaffinity chromatography. In some embodiments the polypeptides of the invention may further comprise a tag to aid in purification, such as a His-tag, which may be subsequently removed, e.g. by way of a cleavage site, such as a TEV cleavage site, engineered between the tag and polypeptide.

In one embodiment, a glycosylated polypeptide produced by a cell may be secreted by the cell into the culture medium and thus the glycosylated polypeptide may be isolated by harvesting the culture medium with or without filtration in order to remove cells and other solid material. Alternatively, the glycosylated polypeptide may be retained by the cell (for example, intracellularly or bound to the surface of the cell) and the glycosylated polypeptide may be isolated by lysis of the cell, for example, through physical disruption by glass beads and/or exposure to high pH conditions and subsequent filtration.

In addition to increased sialylation levels, a polypeptide of the invention may also be characterised by increased mannosylation. The term "increased mannosylation" encompasses an increase in the number of mannose groups conjugated to each polypeptide molecule and/or to an increase in the number of polypeptide molecules (e.g. produced in the method/use of the invention) that have mannose conjugated thereto. Preferably, the term "increased mannosylation" encompasses an increase in the number of mannose groups conjugated to each polypeptide molecule and to an increase in the number of polypeptide molecules (e.g. produced in the method/use of the invention) that have mannose conjugated thereto. The mannose is a component of a glycan conjugated to a glycosylated polypeptide. The number of mannose groups conjugated to each polypeptide molecule and/or to the number of polypeptide molecules that have mannose conjugated thereto may be referred to herein as the "mannosylation level".

Mannosylation may be increased when compared to the mannosylation of the same glycosylated polypeptide produced under the same conditions (e.g. using the same cell line) but wherein the cell has not been contacted with kifunensine. Thus, to determine when mannosylation is increased, the skilled person can compare the mannosylation level of a polypeptide produced in accordance with a method or use of the invention with the same glycosylated polypeptide produced under the same conditions (e.g. using the same cell line) but wherein the cell has not been contacted with kifunensine.

A mannosylation level may be conveniently expressed as a % mannosylation level. In one embodiment, mannosylation is increased by at least 5%, 10%, 20%, 30%, 40% or 50% when compared to the mannosylation of the same glycosylated polypeptide produced under the same conditions (e.g. using the same cell line) but wherein the cell has not been contacted with kifunensine.

In one embodiment the increase in mannosylation is statistically-significant.

A method or use of the invention is preferably carried out in vitro.

In one aspect the invention provides a glycosylated polypeptide obtainable by a method of the invention.

The term "obtainable" as used herein also encompasses the term "obtained". In one embodiment the term "obtainable" means obtained.

A glycosylated polypeptide obtainable by the method of the invention may have a desired glycosylation profile, for example, a glycosylation profile identical to or closely matching that of a reference glycosylated polypeptide. In one embodiment, the glycosylated polypeptide obtainable by a method of the invention comprises increased sialylation and increased mannosylation. In one embodiment, the glycosylated polypeptide obtainable by a method of the invention comprises increased sialylation and increased mannosylation compared to the same glycosylated polypeptide produced under the same conditions in the absence of kifunensine.

The glycosylated polypeptide of the present invention may take the form of a pharmaceutical composition. Thus, in one aspect the invention also provides a pharmaceutical composition comprising: a glycosylated polypeptide of the invention; and a pharmaceutically acceptable carrier, excipient, and/or salt. A pharmaceutically acceptable carrier, excipient, and/or salt may facilitate processing of the glycosylated polypeptide into preparations suitable for pharmaceutical administration.

Oral formulations may include pharmaceutically acceptable carriers known in the art in dosages suitable for oral administration. Such carriers enable the compositions to be formulated as tablets, pills, dragees, capsules, liquids, gels, syrups, slurries, suspensions, and the like suitable for ingestion by the subject.

Formulation for oral use can be obtained through combination of active compounds with a solid excipient, optionally grinding a resulting mixture, and processing the mixture of granules, after adding suitable additional compounds if desired to obtain tablets or dragee cores. Suitable excipients include carbohydrate or protein fillers such as sugars, including lactose, sucrose, mannitol, sorbitol; starch from corn, wheat, rice, potato, or other plants;

cellulose such as methylceilulose, hydroxypropylmethylcellulose, or sodium carboxymethylcellulose; and gums including arabic and tragacanth; as well as proteins such as gelatin and collagen. If desired, disintegrating or solubilising agents may be added, such as cross linked polyvinyl pyrrolidone, agar, alginic acid, or a salt thereof.

Dragee cores can be provided with suitable coatings such as concentrated sugar solutions, which may also contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for product identification or to characterise the quantity of active compound.

Formulations for oral use include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally stabilisers. In soft capsules, the active compounds can be dissolved or suspended in suitable liquids, such as fatty oils, liquid paraffin, or liquid polyethylene glycol with or without stabilisers.

Formulations for parenteral administration include aqueous solutions of active compounds. For injection, the formulations of the invention may take the form of aqueous solutions, preferably in physiologically compatible buffers such as Hank's solution, Ringer's solution, or physiologically buffered saline. Aqueous suspension injections can contain substances which increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension can also contain suitable stabilisers or agents which increase the solubility of the compounds to allow for the preparation of highly concentrated solutions.

For topical or nasal administration, penetrants appropriate to the particular barrier to be permeated may be used in the formulation.

In one aspect, the invention provides a glycosylated polypeptide or pharmaceutical composition of the invention for use in medicine. The invention also provides use of a glycosylated polypeptide or pharmaceutical composition of the invention in the manufacture of a medicament. The invention also provides a method of treatment comprising administering a glycosylated polypeptide or pharmaceutical composition of the invention to a subject.

In one aspect the invention provides a glycosylated polypeptide or a pharmaceutical composition for use in the treatment of a cancer, an inflammatory disorder, an autoimmune disorder, cardiovascular disorder or an ophthalmologic disorder. In a related aspect, there is provided use of a glycosylated polypeptide or a pharmaceutical composition in the manufacture of a medicament for treating a cancer, an inflammatory disorder, an autoimmune disorder, cardiovascular disorder or an ophthalmologic disorder. Likewise, there is provided a method of treating a cancer, an inflammatory disorder, an autoimmune disorder, cardiovascular disorder or an ophthalmologic disorder, the method comprising administering a glycosylated polypeptide or a pharmaceutical composition of the invention to a subject.

A "subject" may be a mammal, such as a human or other animal. Preferably "subject" means a human subject.

The term "disorder" as used herein also encompasses a "disease". In one embodiment the disorder is a disease.

The term "treat" or "treating" as used herein encompasses prophylactic treatment (e.g. to prevent onset of a disorder) as well as corrective treatment (treatment of a subject already suffering from a disorder). Preferably "treat" or "treating" as used herein means corrective treatment.

The term "treat" or "treating" as used herein refers to the disorder and/or a symptom thereof.

Therefore a glycosylated polypeptide or pharmaceutical composition of the invention may be administered to a subject in a therapeutically effective amount or a prophylactically effective amount.

A "therapeutically effective amount" is any amount of the glycosylated polypeptide or pharmaceutical composition, which when administered alone or in combination to a subject for treating said disorder (or a symptom thereof) is sufficient to effect such treatment of the disorder, or symptom thereof.

A "prophylactically effective amount" is any amount of the glycosylated polypeptide or pharmaceutical composition that, when administered alone or in combination to a subject inhibits or delays the onset or reoccurrence of a disorder (or a symptom thereof). In some embodiments, the prophylactically effective amount prevents the onset or reoccurrence of a disorder entirely. "Inhibiting" the onset means either lessening the likelihood of a disorder's onset (or symptom thereof), or preventing the onset entirely.

Administration of the glycosylated polypeptide or pharmaceutical composition of the invention may be accomplished orally or parenterally.

In a particularly preferred embodiment the formulation is administered parenterally. Methods of parenteral delivery include topical, intra-arterial, intramuscular, subcutaneous, intramedullary, intrathecal, intra-ventricular, intravenous, intraperitoneal, or intranasal administration.

The optimal dosage will be determined by the clinician. The precise dosage to be administered may be varied depending on such factors as the age, sex and weight of the subject, the method and formulation of administration, as well as the nature and severity of the disorder to be treated. Other factors such as diet, time of administration, condition of the subject, drug combinations, and reaction sensitivity may be taken into account. An effective treatment regimen may be determined by the clinician responsible for the treatment. One or more administrations may be given, and typically the benefits are observed after a series of at least three, five, or more administrations. Repeated administration may be desirable to maintain the beneficial effects of the composition.

The treatment may be administered by any effective route, such as by subcutaneous injection, although alternative routes which may be used include intramuscular or intralesional injection, oral, aerosol, parenteral, topical or via a suppository.

The treatment may be administered as a liquid formulation, although other formulations may be used. For example, the treatment may be mixed with suitable pharmaceutically acceptable carriers, and may be formulated as solids (tablets, pills, capsules, granules, etc) in a suitable composition for oral, topical or parenteral administration. Most preferably, the formulation is administered subcutaneously.

Embodiments related to the various uses of the invention are intended to be applied equally to the methods, glycosylated polypeptides, pharmaceutical compositions, therapeutic uses/methods, and vice versa.

Sequence Homology

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art. Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position-Specific Gap Penalties and Weight Matrix Choice, 22(22) Nucleic Acids Research 4673-4680 (1994); and iterative refinement, see, e.g., Osamu Gotoh, Significant Improvement in Accuracy of Multiple Protein. Sequence Alignments by Iterative Refinement as Assessed by Reference to Structural Alignments, 264(4) J. Mol. Biol. 823-838 (1996). Local methods align sequences by identifying one or more conserved motifs shared by all of the input sequences. Non-limiting methods include, e.g., Match-box, see, e.g., Eric Depiereux and Ernest Feytmans, Match-Box: A Fundamentally New Algorithm for the Simultaneous Alignment of Several Protein Sequences, 8(5) CABIOS 501-509 (1992); Gibbs sampling, see, e.g., C. E. Lawrence et al., Detecting Subtle Sequence Signals: A Gibbs Sampling Strategy for Multiple Alignment, 262(5131) Science 208-214 (1993); Align-M, see, e.g., Ivo Van Walle et al., Align-M-A New Algorithm for Multiple Alignment of Highly Divergent Sequences, 20(9) Bioinformatics:1428-1435 (2004).

Thus, percent sequence identity is determined by conventional methods. See, for example, Altschul et al., Bull. Math. Bio. 48: 603-16, 1986 and Henikoff and Henikoff, Proc. Natl. Acad. Sci. USA 89:10915-19, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown below (amino acids are indicated by the standard one-letter codes).

The "percent sequence identity" between two or more nucleic acid or amino acid sequences is a function of the number of identical positions shared by the sequences. Thus, % identity may be calculated as the number of identical nucleotides/amino acids divided by the total number of nucleotides/amino acids, multiplied by 100. Calculations of % sequence identity may also take into account the number of gaps, and the length of each gap that needs to be introduced to optimize alignment of two or more sequences. Sequence comparisons and the determination of percent identity between two or more sequences can be carried out using specific mathematical algorithms, such as BLAST, which will be familiar to a skilled person.

Alignment Scores for Determining Sequence Identity

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | −1 | 5 | | | | | | | | | | | | | | | | | | |
| N | −2 | 0 | 6 | | | | | | | | | | | | | | | | | |
| D | −2 | −2 | 1 | 6 | | | | | | | | | | | | | | | | |
| C | 0 | −3 | −3 | −3 | 9 | | | | | | | | | | | | | | | |
| Q | −1 | 1 | 0 | 0 | −3 | 5 | | | | | | | | | | | | | | |
| E | −1 | 0 | 0 | 2 | −4 | 2 | 5 | | | | | | | | | | | | | |
| G | 0 | −2 | 0 | −1 | −3 | −2 | −2 | 6 | | | | | | | | | | | | |
| H | −2 | 0 | 1 | −1 | −3 | 0 | 0 | −2 | 8 | | | | | | | | | | | |
| I | −1 | −3 | −3 | −3 | −1 | −3 | −3 | −4 | −3 | 4 | | | | | | | | | | |
| L | −1 | −2 | −3 | −4 | −1 | −2 | −3 | −4 | −3 | 2 | 4 | | | | | | | | | |
| K | −1 | 2 | 0 | −1 | −3 | 1 | 1 | −2 | −1 | −3 | −2 | 5 | | | | | | | | |
| M | −1 | −1 | −2 | −3 | −1 | 0 | −2 | −3 | −2 | 1 | 2 | −1 | 5 | | | | | | | |
| F | −2 | −3 | −3 | −3 | −2 | −3 | −3 | −3 | −1 | 0 | 0 | −3 | 0 | 6 | | | | | | |
| P | −1 | −2 | −2 | −1 | −3 | −1 | −1 | −2 | −2 | −3 | −3 | −1 | −2 | −4 | 7 | | | | | |
| S | 1 | −1 | 1 | 0 | −1 | 0 | 0 | 0 | −1 | −2 | −2 | 0 | −1 | −2 | −1 | 4 | | | | |
| T | 0 | −1 | 0 | −1 | −1 | −1 | −1 | −2 | −2 | −1 | −1 | −1 | −1 | −2 | −1 | 1 | 5 | | | |
| W | −3 | −3 | −4 | −4 | −2 | −2 | −3 | −2 | −2 | −3 | −2 | −3 | −1 | 1 | −4 | −3 | −2 | 11 | | |
| Y | −2 | −2 | −2 | −3 | −2 | −1 | −2 | −3 | 2 | −1 | −1 | −2 | −1 | 3 | −3 | −2 | −2 | 2 | 7 | |
| V | 0 | −3 | −3 | −3 | −1 | −2 | −2 | −3 | −3 | 3 | 1 | −2 | 1 | −1 | −2 | −2 | 0 | −3 | −1 | 4 |

The percent identity is then calculated as:

$$\frac{\text{Total number of identical matches}}{\left[\begin{array}{c}\text{length of the longer sequence plus the number of}\\ \text{gaps introduced into the longer sequence in}\\ \text{order to align the two sequences}\end{array}\right]}\times 100$$

Substantially homologous polypeptides are characterized as having one or more amino acid substitutions, deletions or additions. These changes are preferably of a minor nature, that is conservative amino acid substitutions (see below) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20-25 residues, or an affinity tag.

Conservative Amino Acid Substitutions

Basic: arginine
lysine
histidine
Acidic: glutamic acid
aspartic acid
Polar: glutamine
asparagine
Hydrophobic: leucine
isoleucine
valine
Aromatic: phenylalanine
tryptophan
tyrosine
Small: glycine
alanine
serine
threonine
methionine In addition to the 20 standard amino acids, non-standard amino acids (such as 4-hydroxyproline, 6-N-methyl lysine, 2-aminoisobutyric acid, isovaline and α-methyl serine) may be substituted for amino acid residues of the polypeptides of the present invention. A limited number of non-conservative amino acids, amino acids that are not encoded by the genetic code, and unnatural amino acids may be substituted for polypeptide amino acid residues. The polypeptides of the present invention can also comprise non-naturally occurring amino acid residues.

Non-naturally occurring amino acids include, without limitation, trans-3-methylproline, 2,4-methano-proline, cis-4-hydroxyproline, trans-4-hydroxy-proline, N-methylglycine, allo-threonine, methyl-threonine, hydroxy-ethylcysteine, hydroxyethylhomo-cysteine, nitro-glutamine, homoglutamine, pipecolic acid, tert-leucine, norvaline, 2-azaphenylalanine, 3-azaphenyl-alanine, 4-azaphenyl-alanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell free system comprising an *E. coli* S30 extract and commercially available enzymes and other reagents. Proteins are purified by chromatography. See, for example, Robertson et al., J. Am. Chem. Soc. 113:2722, 1991; Ellman et al., Methods Enzymol. 202:301, 1991; Chung et al., Science 259:806-9, 1993; and Chung et al., Proc. Natl. Acad. Sci. USA 90:10145-9, 1993). In a second method, translation is carried out in *Xenopus* oocytes by microinjection of mutated mRNA and chemically aminoacylated suppressor tRNAs (Turcatti et al., J. Biol. Chem. 271:19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenyl-alanine, 4-azaphenylalanine, or 4-fluorophenylalanine). The non-naturally occurring amino acid is incorporated into the polypeptide in place of its natural counterpart. See, Koide et al., Biochem. 33:7470-6, 1994. Naturally occurring amino acid residues can be converted to non-naturally occurring species by in vitro chemical modification. Chemical modification can be combined with site-directed mutagenesis to further expand the range of substitutions (Wynn and Richards, Protein Sci. 2:395-403, 1993).

A limited number of non-conservative amino acids, amino acids that are not encoded by the genetic code, non-naturally occurring amino acids, and unnatural amino acids may be substituted for amino acid residues of polypeptides of the present invention.

Essential amino acids in the polypeptides of the present invention can be identified according to procedures known in the art, such as site-directed mutagenesis or alanine-scanning mutagenesis (Cunningham and Wells, Science 244: 1081-5, 1989). Sites of biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306-12, 1992; Smith et al., J. Mol. Biol. 224:899-904, 1992; Wlodaver et al., FEBS Lett. 309:59-64, 1992. The identities of essential amino acids can also be inferred from analysis of homologies with related components (e.g. the translocation or protease components) of the polypeptides of the present invention.

Multiple amino acid substitutions can be made and tested using known methods of mutagenesis and screening, such as those disclosed by Reidhaar-Olson and Sauer (Science 241: 53-7, 1988) or Bowie and Sauer (Proc. Natl. Acad. Sci. USA 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., Biochem. 30:10832-7, 1991; Ladner et al., U.S. Pat. No. 5,223,409; Huse, WIPO Publication WO 92/06204) and region-directed mutagenesis (Derbyshire et al., Gene 46:145, 1986; Ner et al., DNA 7:127, 1988).

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide the skilled person with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure.

Amino acids are referred to herein using the name of the amino acid, the three letter abbreviation or the single letter abbreviation. The term “protein”, as used herein, includes proteins, polypeptides, and peptides. As used herein, the term “amino acid sequence” is synonymous with the term “polypeptide” and/or the term “protein”. In some instances, the term “amino acid sequence” is synonymous with the term “peptide”. In some instances, the term “amino acid sequence" is synonymous with the term "enzyme". The terms "protein" and "polypeptide" are used interchangeably herein. In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Other definitions of terms may appear throughout the specification. Before the exemplary embodiments are described in more detail, it is to be understood that this disclosure is not limited to particular embodiments described, and as such may vary. It is also to be understood that the terminology used herein is for the purpose of describing particular embodiments only, and is not intended to be limiting, since the scope of the present disclosure will be defined only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "a glycosylated polypeptide" includes a plurality of such candidate agents and reference to "the glycosylated polypeptide" includes reference to one or more glycosylated polypeptides and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

BRIEF DESCRIPTION OF THE DRAWINGS

Embodiments of the invention will now be described, by way of example only, with reference to the following Figures and Examples.

SEQUENCE LISTING

SEQ ID NO: 1-Golimumab Heavy Chain IgG1 (the sinqle glycosylation site at amino acid position 306 is shown in bold and underlined)

QVQLVESGGG VVQPGRSLRL SCAASGFIFS SYAMHWVRQA PGNGLEWVAF
MSYDGSNKKY ADSVKGRFTI SRDNSKNTLY LQMNSLRAED TAVYYCARDR
GIAAGGNYYY YGMDVWGQGT TVTVSSASTK GPSVFPLAPS SKSTSGGTAA
LGCLVKDYFP EPVTVSWNSG ALTSGVHTFP AVLQSSGLYS LSSVVTVPSS
SLGTQTYICN VNHKPSNTKV DKKVEPKSCD KTHTCPPCPA PELLGGPSVF
LFPPKPKDTL MISRTPEVTC VVVDVSHEDP EVKFNWYVDG VEVHNAKTKP
REEQYNSTYR VVSVLTVLHQ DWLNGKEYKC KVSNKALPAP IEKTISKAKG
QPREPQVYTL PPSRDELTKN QVSLTCLVKG FYPSDIAVEW ESNGQPENNY
KTTPPVLDSD GSFFLYSKLT VDKSRWQQGN VFSCSVMHEA LHNHYTQKSL
SLSPGK

SEQ ID NO: 2-Golimumab Liqht Chain

EIVLTQSPAT LSLSPGERAT LSCRASQSVY SYLAWYQQKP GQAPRLLIYD
ASNRATGIPA RFSGSGSGTD FTLTISSLEP EDFAVYYCQQ RSNWPPFTFG
PGTKVDIKRT VAAPSVFIFP PSDEQLKSGT ASVVCLLNNF YPREAKVQWK
VDNALQSGNS QESVTEQDSK DSTYSLSSTL TLSKADYEKH KVYACEVTHQ
GLSSPVTKSF NRGEC

SEQ ID NO: 3-Denosumab Heavy Chain IgG2 (the sinqle glycosylation site at amino acid position 298 is shown in bold and underlined)

EVQLLESGGG LVQPGGSLRL SCAASGFTFS SYAMSWVRQA PGKGLEWVSG ITGSGGSTYY
ADSVKGRFTI SRDNSKNTLY LQMNSLRAED TAVYYCAKDP GTTVIMSWFD PWGQGTLVTV
SSASTKGPSV FPLAPCSRST SESTAALGCL VKDYFPEPVT VSWNSGALTS GVHTFPAVLQ
SSGLYSLSSV VTVPSSNFGT QTYTCNVDHK PSNTKVDKTV ERKCCVECPP CPAPPVAGPS
VFLFPPKPKD TLMISRTPEV TCVVVDVSHE DPEVQFNWYV DGVEVHNAKT KPREEQFNST
FRVVSVLTVV HQDWLNGKEY KCKVSNKGLP APIEKTISKT KGQPREPQVY TLPPSREEMT
KNQVSLTCLV KGFYPSDIAV EWESNGQPEN NYKTTPPMLD SDGSFFLYSK LTVDKSRWQQ
GNVFSCSVMH EALHNHYTQK SLSLSPGK

SEQID NO: 4-Denosumab Light Chain (kappa)

EIVLTQSPGT LSLSPGERAT LSCRASQSVR GRYLAWYQQK PGQAPRLLIY
GASSRATGIP DRFSGSGSGT DFTLTISRLE PEDFAVFYCQ QYGSSPRTFG
QGTKVEIKRT VAAPSVFIFP PSDEQLKSGT ASVVCLLNNF YPREAKVQWK VDNALQSGNS
QESVTEQDSK DSTYSLSSTL TLSKADYEKH KVYACEVTHQ GLSSPVTKSF NRGEC

EXAMPLES

Example 1

Effects of Kifunensine on the Sialylation of Human IgG1 Antibodies Produced in Sp2/0 Cells Murine Sp2/0 cells transfected with expression vectors encoding SEQ ID NOs: 1 and 2 (which correspond to the heavy and light chains respectively of the human anti-TNFα IgG1 monoclonal antibody, golimumab) were cultured in perfusion bioreactors for 30 days under standard operating parameters. To examine the effect of kifunensine on the sialylation levels of the resulting IgG1, the perfusion cultures were supplemented with either 3, 6, 9, or 12 μg/L kifunensine (corresponding to 13 nM, 26 nM, 39 nM or 52 nM). A control culture was also maintained under the same conditions albeit in the absence of kifunensine. No significant impact on cell viability was observed in any of the cultures supplemented with kifunensine.

Figure 1:
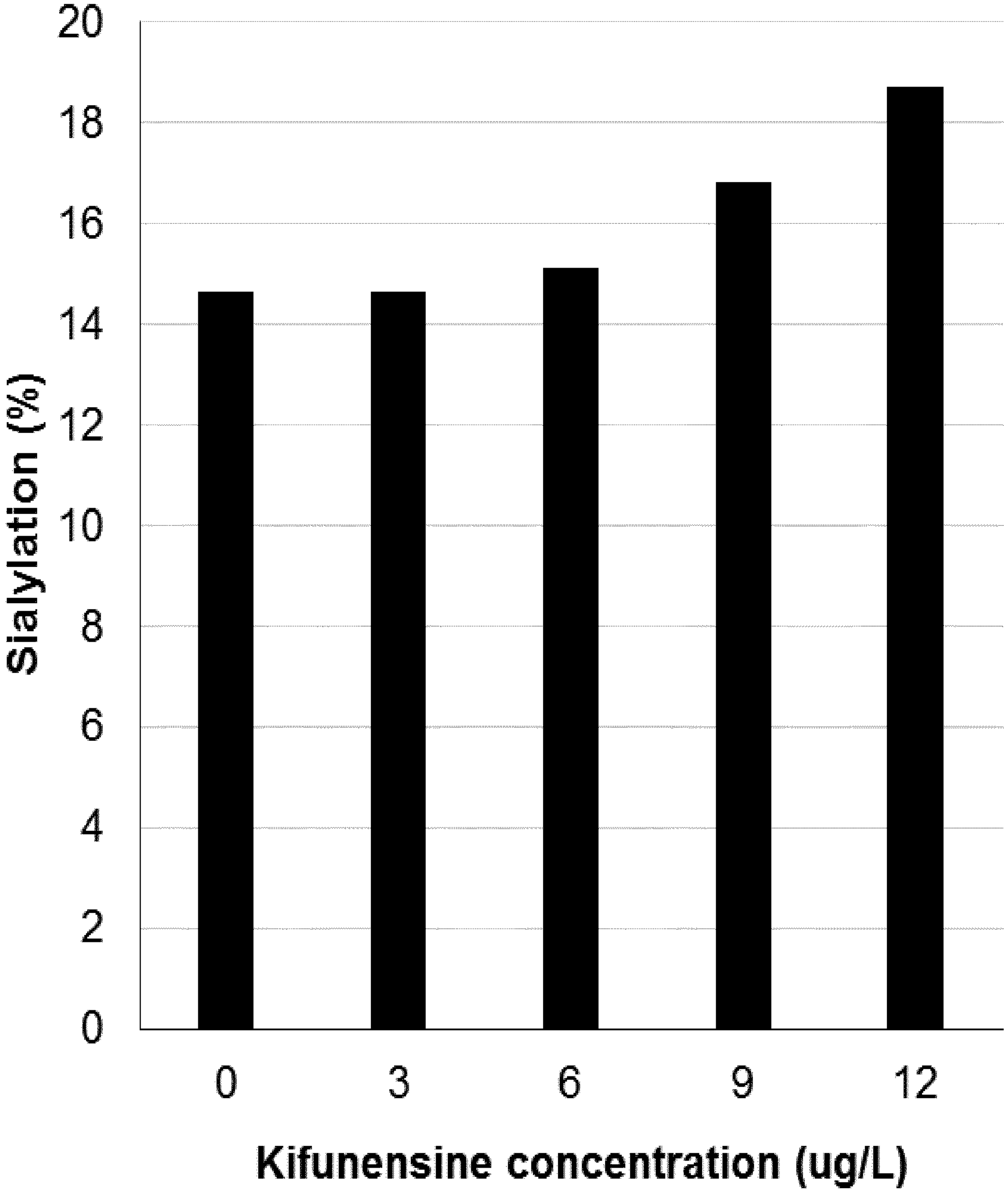
FIG. 1 shows percentage sialylation of IgG1 monoclonal antibodies produced in Sp2/0 cells supplemented with either 3, 6, 9 or 12 μg/L kifunensine.

On culture day 18, samples were taken from the perfusion bioreactors and the percentage sialylation of the IgG1 antibodies was determined by glycan analysis. Briefly, antibodies were first purified using protein A chromatography, glycans were then enzymatically released from the antibody, fluorescently labelled with 2-aminobenzamide and analysed using hydrophilic interaction chromatography (HILIC) based methods. As shown in FIG. 1, an increase in sialylation compared to control was evident in cultures supplemented with 6 μg/L kifunensine and above, particularly 9 and 12 μg/L kifunensine. Peak sialylation levels were seen with 12 μg/L kifunensine (~52 nM).

Example 2

Effects of Kifunensine on Fc-Glycan Sialylation of Human IgG2 Antibodies Produced in CHO Cells CHO cells transfected with expression vectors encoding SEQ ID NOs: 3 and 4 (which correspond to the heavy and lights chains respectively of the human anti-RANKL IgG2 monoclonal antibody, denosumab) were cultured in bioreactors using standard fed-batch methods. To examine the effects of kifunensine on the Fc-glycan sialylation levels of the resulting IgG2, the cultures were supplemented with either 30, 40, 50 or 60 nM kifunensine on day 3 of the culture. A control culture was also maintained under the same conditions albeit in the absence of kifunensine. No significant impact on cell viability was observed in any of the cultures supplemented with kifunensine.

Figure 2:
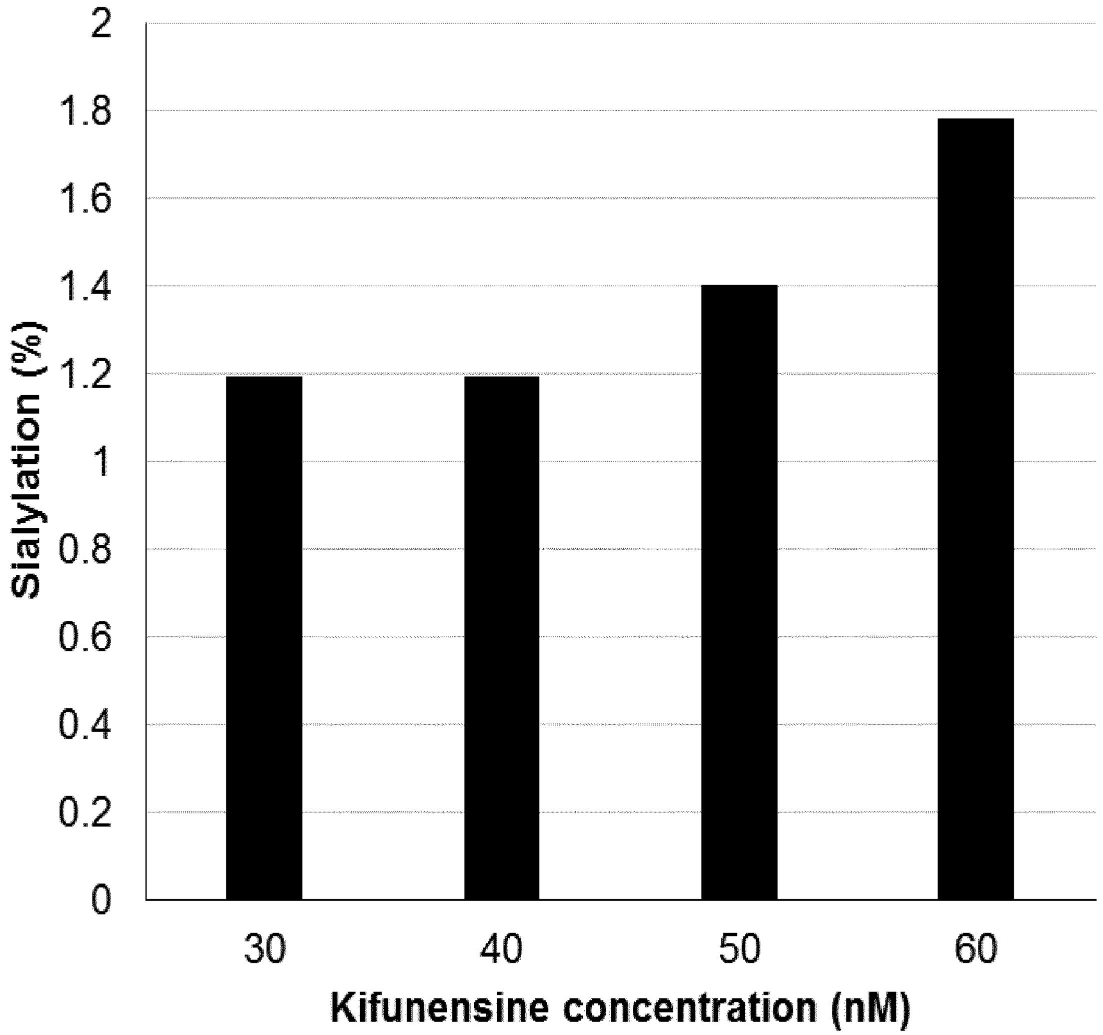
FIG. 2 shows percentage sialylation of IgG2 monoclonal antibodies produced in CHO cells supplemented with 30, 40, 50 or 60 nM kifunensine.

On day 20, samples were taken from bioreactors and the percentage Fc-glycan sialylation of the IgG2 antibodies was determined as described in Example 1. As shown in FIG. 2, an increase in Fc-glycan sialylation compared to control was evident when supplemented with >40 nM kifunensine. Peak Fc-glycan sialylation was observed in cultures supplemented with 60 nM kifunensine.

Example 3

Effects of Kifunensine on Sialylation of EPO Produced in CHO Cells

CHO cells transfected with expression vectors encoding recombinant human EPO (UniProt Accession No. P01588, Sequence Version 1, Entry Version 195) are cultured in perfusion bioreactors for 18 days under standard operating parameters. The culture medium is supplemented with 12 μg/L kifunensine from day 0.

Recombinant human EPO produced during the culture period is harvested throughout the production phase and at the end of the culture period, a sample is obtained to determine the glycosylation profile. The resultant recombinant human EPO has increased mannosylation and sialylation compared to that produced in cultures without kifunensine.

Clauses

1. Use of kifunensine for increasing sialylation of a glycosylated polypeptide, wherein a cell that produces the glycosylated polypeptide is contacted with kifunensine.

2. A method for increasing sialylation of a glycosylated polypeptide, the method comprising:
   a. providing a cell that produces the glycosylated polypeptide; and
   b. contacting the cell with kifunensine, thereby increasing sialylation of the glycosylated polypeptide produced by the cell.

3. A method for producing a glycosylated polypeptide having increased sialylation, the method comprising:
   a. providing a cell that produces the glycosylated polypeptide; and
   b. contacting the cell with kifunensine, thereby producing the glycosylated polypeptide having increased sialylation.

4. The use according to clause 1 or the method according to clause 2 or 3, further comprising isolating the glycosylated polypeptide.

5. The use or method according to any one of the preceding clauses, wherein the cell is contacted with kifunensine prior to production of the glycosylated polypeptide by the cell.

6. The use or method according to any one of clauses 1-4, wherein the cell is contacted with kifunensine during production of the glycosylated polypeptide by the cell.

7. The use or method according to any one of the preceding clauses, wherein the cell is contacted with a solution (e.g. culture medium) comprising kifunensine at a concentration of about 30-150 nM.

8. The use or method according to any one of the preceding clauses, wherein the cell is contacted with a solution (e.g. culture medium) comprising kifunensine at a concentration of about 35-75 nM.

9. The use or method according to any one of the preceding clauses, wherein the cell is contacted with a solution (e.g. culture medium) comprising kifunensine at a concentration of about 40-60 nM.

10. The use or method according to any one of the preceding clauses, wherein the cell is contacted with a solution (e.g. culture medium) comprising kifunensine at a concentration of about 50 nM.

11. The use or method according to any one of the preceding clauses, wherein the glycosylated polypeptide is characterised by increased mannosylation.

12. The use or method according to any one of the preceding clauses, wherein the glycosylated polypeptide is a recombinant glycosylated polypeptide.

13. The use or method according to any one of the preceding clauses, wherein the glycosylated polypeptide is a human glycosylated polypeptide.

14. The use or method according to any one of the preceding clauses, wherein the glycosylated polypeptide is an antibody, an antigen-binding portion of an antibody, a hormone, an Fc-fusion polypeptide, an albumin fusion polypeptide, an enzyme, or a cytokine.

15. The use or method according to clause 14, wherein the Fc-fusion polypeptide is abatacept, afilbercept, alefacept, belatacept, etarnecept or rilonacept.

16. The use or method according to clause 14, wherein the hormone is erythropoietin, parathyroid hormone, growth hormone, insulin, glucagon, follicle stimulating hormone, luteinizing hormone or choriogonadotropin.

17. The use or method according to any one of the preceding clauses, wherein the glycosylated polypeptide is a monoclonal antibody or antigen-binding portion thereof.

18. The use or method according to any one of the preceding clauses, wherein the glycosylated polypeptide is an IgG1 antibody or antigen-binding portion thereof, or an IgG2 antibody or antigen-binding portion thereof.

19. The use or method according to clause 17 or 18, wherein the antibody or antigen-binding fragment thereof is adalimumab, abciximab, alemtuzumab, atezolizumab, avelumab, basiliximab, bevacizumab, brodalumab, certolizumab, cetuximab, daratumumab, daclizumab, denosumab. dupilumab, durvalumab, eculizumab, efalizumab, gemtuzumab, golimumab, guselkumab, ibritumomab, infliximab, ixekizumab, muromonab-CD3, natalizumab, nivolumab, omalizumab, palivizumab; panitumumab, pembrolizumab, ranibizumab, risankizumab, rituximab, secukinumab, tildrakizumab, tocilizumab, tositumomab, trastuzumab, ustekinumab or vedolizumab.

20. The use or method according to any one of the preceding clauses, wherein the glycosylated polypeptide comprises at least one N-linked glycan.

21. The use or method according to any one of the preceding clauses, wherein the glycosylated polypeptide is an antibody, and wherein the Fc portion thereof comprises at least one N-linked glycan.

22. The use or method according to clause 20 or 21, wherein the N-linked glycan is a bi-antennary glycan.

23. The use or method according to any one of the preceding clauses, wherein the cell is a mammalian cell.

24. The use or method according to any one of the preceding clauses, wherein the cell is a rodent cell, a human cell or a non-human primate cell.

25. The use or method according to any one of the preceding clauses, wherein the cell is a Chinese Hamster Ovary (CHO) cell or a murine myeloma cell (Sp2/0).

26. A glycosylated polypeptide obtainable by the method according to any one of clauses 2-25, optionally wherein the glycosylated polypeptide comprises increased sialylation and increased mannosylation.

27. A pharmaceutical composition comprising the glycosylated polypeptide according to clause 26 and a pharmaceutically acceptable carrier, excipient, adjuvant, and/or salt.

28. A glycosylated polypeptide according to clause 26 or the pharmaceutical composition according to clause 27 for use in medicine.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A method comprising:

a. providing a cell that produces a glycosylated polypeptide; and b. contacting the cell in a fed-batch culture system or a perfusion culture system with a solution comprising kifunensine at a concentration of 25-75 nM, thereby producing a glycosylated polypeptide having sialylation.

2. The method of claim 1, further comprising isolating the glycosylated polypeptide.

3. The method according to claim 1, wherein the cell is contacted with kifunensine prior to production of the glycosylated polypeptide by the cell, or wherein the cell is contacted with kifunensine during production of the glycosylated polypeptide by the cell.

4. The method according to claim 1, wherein the cell is contacted with a solution comprising kifunensine at a concentration of 50-60 nM.

5. The method according to claim 1, wherein the glycosylated polypeptide is characterised by increased mannosylation.

6. The method according to claim 1, wherein the glycosylated polypeptide is a recombinant glycosylated polypeptide.

7. The method according to claim 6, wherein the glycosylated polypeptide is a human glycosylated polypeptide, and/or wherein the glycosylated polypeptide is an antibody, an antigen-binding portion of an antibody, a hormone, an Fc-fusion polypeptide, an albumin fusion polypeptide, an enzyme, or a cytokine.

8. The method according to claim 7, wherein the Fc-fusion polypeptide is abatacept, aflibercept, alefacept, belatacept, etanercept or rilonacept, or wherein the hormone is erythropoietin, parathyroid hormone, growth hormone, insulin, glucagon, follicle stimulating hormone, luteinizing hormone or choriogonadotropin.

9. The method according to claim 1, wherein the glycosylated polypeptide is a monoclonal antibody or antigen-binding portion thereof, and/or wherein the glycosylated polypeptide is an IgG1 antibody or antigen-binding portion thereof, or an IgG2 antibody or antigen-binding portion thereof.

10. The method according to claim 9, wherein the antibody or antigen-binding portion thereof is adalimumab, abciximab, alemtuzumab, atezolizumab, avelumab, basiliximab, bevacizumab, brodalumab, certolizumab, cetuximab, daratumumab, daclizumab, denosumab, dupilumab, durvalumab, eculizumab, efalizumab, gemtuzumab, golimumab, guselkumab, ibritumomab, infliximab, ixekizumab, muromonab-CD3, natalizumab, nivolumab, omalizumab, palivizumab, panitumumab, pembrolizumab, ranibizumab, risankizumab, rituximab, secukinumab, tildrakizumab, tocilizumab, tositumomab, trastuzumab, ustekinumab or vedolizumab.

11. The method according to claim 1, wherein the glycosylated polypeptide comprises at least one N-linked glycan, and/or wherein the glycosylated polypeptide is an antibody, and wherein the Fc portion thereof comprises at least one N-linked glycan, preferably wherein the N linked glycan is a bi antennary glycan.

12. The method according to claim 11, wherein the N-linked glycan is a bi-antennary glycan.

13. The method according to claim 1, wherein the cell is a mammalian cell.

14. The method according to claim 13, wherein the mammalian cell is a rodent cell, a human cell or a non-human primate cell.

15. The method according to claim 13, wherein the mammalian cell is a Chinese Hamster Ovary (CHO) cell or a murine myeloma cell (Sp2/0).

16. The method according to claim 1, wherein the solution is a culture medium.

17. The method according to claim 1, wherein the cell is contacted with a solution comprising kifunensine at a concentration of about 50 nM.

* * * * *